United States Patent
Gluckman et al.

(10) Patent No.: US 6,665,562 B2
(45) Date of Patent: Dec. 16, 2003

(54) ADAPTIVE ELECTRIC FIELD MODULATION OF NEURAL SYSTEMS

(75) Inventors: Bruce J. Gluckman, Arlington, VA (US); Steven J. Schiff, Bethesda, MD (US)

(73) Assignee: George Mason University, Fairfax, VA (US)

( * ) Notice: Subject to any disclaimer, the term of this patent is extended or adjusted under 35 U.S.C. 154(b) by 269 days.

(21) Appl. No.: 09/729,929

(22) Filed: Dec. 6, 2000

(65) Prior Publication Data

US 2001/0029391 A1 Oct. 11, 2001

Related U.S. Application Data

(60) Provisional application No. 60/169,280, filed on Dec. 7, 1999.

(51) Int. Cl.[7] .................................................. A66N 1/40
(52) U.S. Cl. .............................. 607/2; 607/45; 128/898
(58) Field of Search ................................ 607/2, 45, 116, 607/148; 600/378, 545; 128/898

(56) References Cited

U.S. PATENT DOCUMENTS

| | | |
|---|---|---|
| 3,850,161 A | 11/1974 | Liss |
| 5,496,258 A | 3/1996 | Anninos et al. |
| 5,522,863 A | 6/1996 | Spano et al. |
| 5,626,145 A | 5/1997 | Clapp et al. |
| 5,697,883 A | 12/1997 | Anninos et al. |
| 5,713,923 A | 2/1998 | Ward et al. |

(List continued on next page.)

OTHER PUBLICATIONS

Bruce J. Gluckman et al., "Stochastic Resonance in a Neuronal Network from Mammalian Brain", Physical Review Letters, vol. 77, No. 19, pp. 4098–4101 (1996).

(List continued on next page.)

*Primary Examiner*—Tu Ba Hoang
(74) *Attorney, Agent, or Firm*—Millen, White, Zelano & Branigan, P.C.

(57) ABSTRACT

The present invention relates to devices and methods of modifying the neuronal activity of a neural system comprising neurons, comprising, one or more of the following steps, measuring the neuronal activity of a neural system; and applying an oriented electric field to the neural system effective to modify the neuronal activity of the neural system, wherein the magnitude and polarity of the applied electric field is changed in response to the measured neuronal activity. The present invention also relates to devices and methods for treating brain disorders, such as epilepsy and Parkinson's disease, comprising, one or more of the following steps, applying a sub-threshold and oriented electric field in situ to the brain of a patient having such a disorder in an amount effective to reduce the abnormal activity of the brain, wherein the electric field is applied through field electrodes in contact with the brain. The present invention also relates to methods and devices for restoring or repairing a brain function, such as sensation (e.g., taste, or smell), somatic activity, auditory activity, visual activity, or motor activity. It can also be used for testing drugs, pharmacological agents, and other modulators of neuronal function.

11 Claims, 9 Drawing Sheets

U.S. PATENT DOCUMENTS

| | | |
|---|---|---|
| 5,752,979 A | 5/1998 | Benabid |
| 5,797,965 A | 8/1998 | Spano et al. |
| 5,800,459 A | 9/1998 | Spano et al. |
| 5,857,978 A | 1/1999 | Hively et al. |
| 5,938,689 A | 8/1999 | Fischell et al. |
| 5,995,868 A | 11/1999 | Dorfmeister et al. |
| 6,016,449 A | 1/2000 | Fischell et al. |
| 6,018,682 A | 1/2000 | Rise |
| 6,061,593 A | 5/2000 | Fischell et al. |
| 6,128,538 A | 10/2000 | Fischell et al. |
| 6,134,474 A | 10/2000 | Fischell et al. |
| 6,161,045 A | 12/2000 | Fischell et al. |
| 6,304,775 B1 | 10/2001 | Iasemidis et al. |
| 6,366,813 B1 | 4/2002 | DiLorenzo |
| 6,374,140 B1 | 4/2002 | Rise |
| 6,480,743 B1 | 11/2002 | Kirkpatrick et al. |
| 6,529,774 B1 * | 3/2003 | Greene .......................... 600/2 |

OTHER PUBLICATIONS

Bruce J. Gluckman et al., "Electric Field Suppression of Epileptiform Activity in Hippocampal Slices", Journal of Neurophysiology, vol. 76, No. 6, pp. 4202–4205 (1996).

M. Velasco et al., Subacute Electrical Stimulation of the Hippocampus Blocks Intractable Temporal Lobe Seizures and Paroxysmal EEG Activities, Epilepsia, 41(2):158–169 (2000).

* cited by examiner

A Top Schematic electrodes: field sense ground sense field

B Side Schematic

Field Orientation
for Suppression

A

Suppressive Control On

B

Excitatory Control On

C

ADAPTIVE ELECTRIC FIELD MODULATION OF NEURAL SYSTEMS

This application claims the benefit of provisional application Ser. No. 60/169,280, filed Dec. 7, 1999, which is hereby incorporated by reference in its entirety.

BACKGROUND OF THE INVENTION

Numerous attempts have been made to suppress epileptic seizures in human patients with indirect electrical stimulation at sites remote from the epileptic focus, including cerebellum (Cooper et al., 1976; Van Buren et al., 1978), thalamus (Cooper et al., 1985; Fisher et al., 1992), and vagal nerve (Murphy et al., 1995; McLachlin, 1997). Surprisingly, there has been far less investigation of the technology required to directly control an epileptic focus electrically. It has been shown that direct current injection into tissue could suppress evoked (Kayyali and Durand, 1991) or spontaneous (Nakagawa and Durand, 1991; Warren and Durand, 1998) epileptiform activity in brain slices. Even simple periodic pacing of a neuronal network with direct electrical stimulation (Kerger and Schiff, 1995) can reduce seizure-like events. In addition, there is some evidence that nonlinear control schemes might be useful in manipulating epileptiform activity (Schiff et al., 1994). In each of these cases, the stimulation was applied in the form of short current pulses directly into the tissue that evoke neuronal firing. Recently, it was demonstrated that steady state (DC) electric fields oriented parallel to pyramidal cells were capable of suppressing epileptic seizure activity in in vitro hippocampal brain slices (Gluckman et al., 1996a). Such field application led to nearly complete suppression of neuronal activity, yet due to a combination of polarization effects (electrode and tissue) and neuronal adaptation, this effect was transient.

DESCRIPTION OF INVENTION

Figure 1:
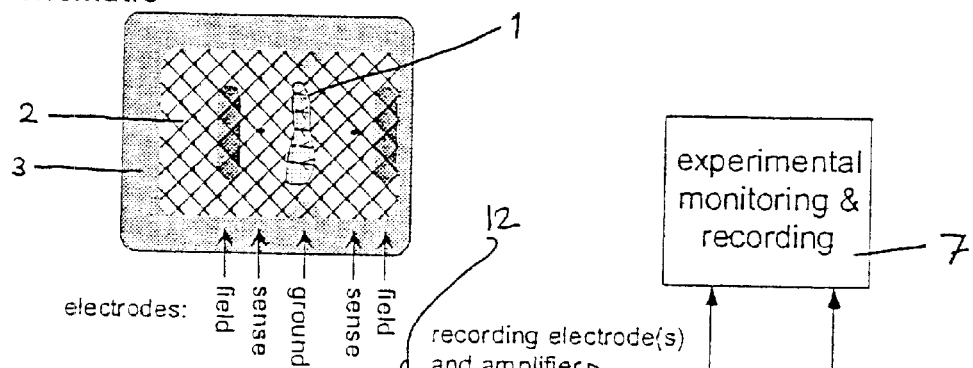
FIG. 1. (A) is a top view schematic drawing of a perfusion chamber used to adaptively modulate the neuronal activity of an isolated neural system. (B) is a side view schematic of the same chamber. The brain slices rest on a nylon mesh just below the upper surface of the perfusate of artificial cerebrospinal fluid (ACSF), and the atmosphere above the perfusate is warmed to the bath temperature of 35° C. and saturated with 95% $O_2$-5% $CO_2$. An electric field is imposed on the slice by a set of Ag—AgCl electrodes embedded in the floor of the chamber. The potential difference applied between parallel plate electrodes F1 and F2 is feedback controlled so that the average field measured at sensing electrodes S1 and S2 is proportional to a program voltage. An additional pair of electrodes, G, are used as recording ground.
Figure 1:
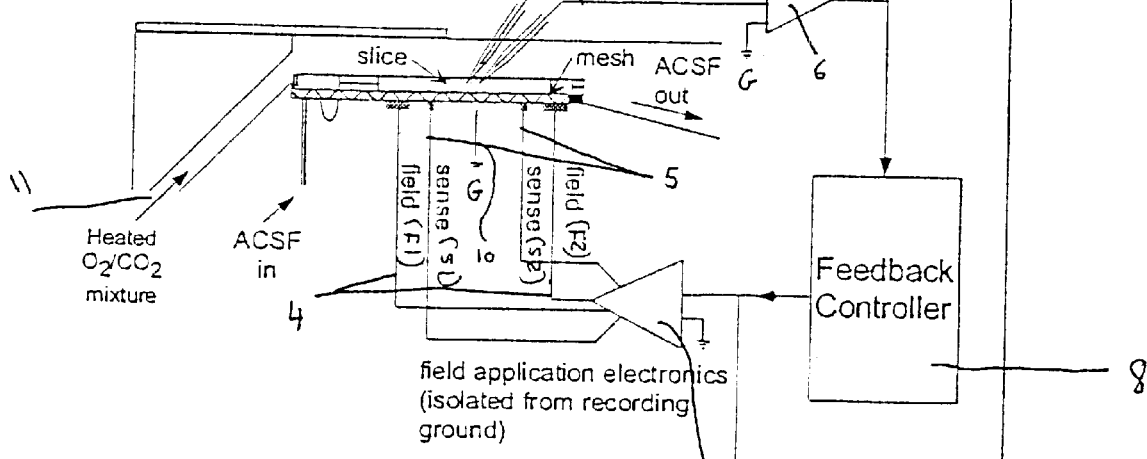
Figure 1:
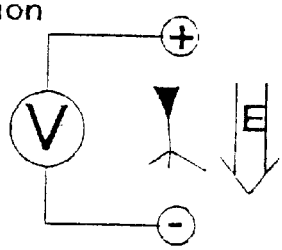

The present invention relates to devices and methods for modulating the neuronal activity of a neural system comprising neurons, such as a brain, brain regions, or any in vivo or in vitro collection of neurons. In particular, the present invention involves the use of applied electric fields to modulate the behavior of a target neural system. In preferred embodiments, the polarity and magnitude of the applied electric field is varied according to information gathered from the modulated neural system, or any other desired source chosen to provide feedback, to modulate the strength of the applied electric field. In such embodiments, preferably a sub-threshold stimulus is administered to modulate to the neural system. The methods and devices of the present invention can be used to treat diseases of the nervous system, to restore neuronal function, paralysis, and motor and sensory deficits, to produce prosthetic devices that interact and modulate neuronal activity, to enhance or suppress neuronal activity and associated phenotypes, and the like.

A preferred method of the present invention relates to modifying the neuronal activity of a neural system comprising neurons, comprising one of more of the following steps, in any order: measuring the neuronal activity, or other behavior, of a neural system; and applying an oriented electric field to said neural system effective to modify the neuronal activity of the neural system, wherein the magnitude and polarity of said applied electric field is changed in response to the measured neuronal activity.

A neural system in accordance with the present invention can be any ensemble of one or more neurons, and/or other excitable cells, such as muscle, heart, retinal, cochlear, tissue culture cells, stem or progenitor cells, including cell-electrode interface devices and the like. Cells can be coupled electrically, chemically, or combinations thereof. The neural system can be an entire brain, ganglia, nerve, etc., or it can be a region or portion of it. Any animal source of material is suitable, including neural systems of invertebrates, such as mollusks, arthropods, insects, etc., vertebrates, such as mammals, humans, non-human mammals, great apes, monkeys, chimpanzees, dogs, cats, rats, mice, etc. In the examples, a specific region of a mammalian brain is dissected out and placed in a chamber where its activity is modified. However, physical isolation of a target brain region is unnecessary; the activity modulation can be performed in situ, as well. Preferred target regions include, but are not limited to, neocortex, sensory cortex, motor cortex, frontal lobe, parietal lobe, occipital lobe, temporal lobe, thalamus, hypothalamus, limbic system, amygdala, septum, hippocampus, fornix, cerebellum, brain stem, medulla, pons, basal ganglia, globus pallidum, striatum, spinal cord, ganglion, cranial nerves, peripheral nerves, retina, cochlea, etc.

In one step of a preferred method, the neuronal activity of the neural system is measured. By the term "neuronal activity," it is meant any measurable physical behavior, output, or phenotype of the system. For example, neurons typically display variations in their membrane potential, such as action potentials, depolarizations, and hyperpolarizations. These changes in the membrane potential can be utilized as a measure of neuronal activity, e.g., by monitoring intracellularly in a single neuron, or extracellularly, the electrical activity of a single neuron or the activity of an ensemble of neurons. Behaviors, or other products of a neural system (e.g., hormones, growth factors, neurotransmitters, ions, etc.) can also be detected, and used as a feedback signal to determine the magnitude and strength of the modulating applied field. For instance, if a purpose is to elicit movement of a limb, then the neuronal activity can be limb motion. The neuronal activity which is measured or assessed can be a subset of the total activity observed in the system, e.g., a particular frequency band of the full neural signal. In the examples, hippocampus slices were monitored for neuronal activity. Although the measuring electrode detected various types of activity, including spontaneous neuronal firing, slow burst activity, and background noise, as well as fast frequency epileptic seizures, it was desired to modulate only the latter. Thus, for these purposes the neuronal activity can be considered to be only the events of interest, e.g., the epileptic seizures.

Methods for measuring and recording neuronal activity can be accomplished according to any suitable method. In preferred embodiments of the invention, the neuronal activity is monitored extracellularly by measuring the extracellular electrical potential of a target population of neurons. Such measurements can reveal complex spikes or burst activity, sharp or slow waves, epileptiform spikes or seizures, arising from one or more neurons in the neural system.

The neuronal activity can be measured by recording the neural system's electrical potential in the extracellular space. The electrodes used to measure the field potential produced by the neural system are referred to as "measuring electrodes" or "recording electrodes." One or more electrodes can be used to measure the field potential. In preferred embodiments, two or more electrodes are utilized. The field potentials recorded at a given extracellular site will depend on a variety of factors, including the location of the electrode(s) with respect to the soma and dendritic layers, the architecture of the neural system, the perfusion solution, etc.

The measuring electrodes can detect the field potential from the applied field as well as the activity generated by the neural system. There are a number of methods that can be used to distinguish the neuronal activity from the applied fields. For example, in in vitro hippocampal slices, a pair of differential electrodes, aligned as closely as possible to the isopotential of the applied field, were used as measuring electrodes. They are "differential" in the sense that an active electrode is placed in the tissue, preferably near the cell body layer of the target neurons, while the reference electrode is placed preferably in the bath external to the tissue. The values obtained from each electrode can be electronically subtracted from each other, reducing background noise. For in vivo use, the differential measuring electrodes can be placed at the same isopotential with respect to the applied field. The electrodes can be as close to the target population as possible, without damaging it. Other methods to reduce noise and the artifact from the applied field can be used as well, either alone, or in combination with the differential electrodes, including filtering and post-processing of the measured signal.

Recording from the electrodes can be performed routinely. For instance, measurements can be made with an AC amplifier if the frequency and number of extracellular bursts are of interest. It can be equipped with filters to cut off frequencies below and above a particular range (band-pass filter) and amplify the signal in preferred ranges, e.g., 50–1000 Hz, preferably, 100–500 Hz. A DC amplifier can also be used, if slower potential changes are of interest.

A method in accordance with the present invention also involves applying an oriented electric field to the neural system effective to modify the neuronal activity of the neural system, preferably where the magnitude and polarity of said applied electric field is changed in response to the measured neuronal activity. Preferably, the applied field is oriented in a particular direction with respect to the somatic-dendritic axis of the neurons in the neural system. Most preferably, the field is parallel to the somatic-dendritic axis. Changing the strength of the applied field in response to a measured activity of the neural system can also be referred to as "adaptive modulation" since the strength of the applied field is adjusted based on an activity value of the neural system (e.g., electrical activity, motor activity, such as limb motion, etc.). A function of the applied electric field is to modify the neuronal activity of the neural system. The electric field is thus applied to the neural system in an amount adequate to change the neuronal behavior of the neural system. Any amount of field which changes the neural system's behavior is an effective applied field. It is believed that a mechanism that underlies adaptive modulation is the ability of the applied field to alter the neuron's excitability by changing its threshold; however, the invention is not bound nor limited to any theory, explanation, or mechanism of how it works.

In preferred methods of the present invention for in vitro applications, two pairs of electrodes can be used in the field application step. A pair of "field electrodes" can be used to produce the applied field. A second pair of electrodes, "sensing electrodes," can be used to measure or sense the field generated by the "field electrodes." The sensing and field electrodes can comprise the same materials described above for the measuring electrodes. In certain applications, however, such as in vivo applications, a field can be applied without sensing electrodes.

In preferred embodiments of the invention, the effective amount of applied field is sub-threshold with respect to the field potential experienced by the neural system. By the term "sub-threshold," it is meant that the amount of applied field or current does not reliably, with 100% probability, initiate new action potentials within the neural system. In contrast, the application of a supra-threshold stimulus reliably, with a high degree of probability, results in neuronal firing. A sub-threshold potential is, for example, less than 100 mV/mm, preferably 50 mV/mm and less, more preferably, 25 mV/mm and less, such as 20 mV/mm, 15 mV/mm, or 10 mV/mm. The sub-threshold potential refers to the potential generated at the level of the target neurons. The amount of potential actually produced by the field electrodes is less important that the field perceived by the target neurons. It is the generated field sensed by the neurons that determines whether a stimulus is sub- or supra-threshold.

In response to the applied electric field, the activity of the neural system can be modified in any desired manner, e.g., the activity can be suppressed, reduced, decreased, diminished, eliminated, counteracted, canceled out, etc., or it can be enhanced, increased, augmented, facilitated, etc. To determine whether the activity of the system has been modified, preferably the same neuronal activity measured in the measurement step is remeasured. Most preferably, the measurement of the neuronal activity is performed simultaneously and continuously with the applied field.

Any effective electrodes can be used for the recording, sensing, and field electrodes, including, e.g., metal, steel, activated iridium, platinum, platinum-iridium, iridium oxide, titanium oxide, silver chloride, gold chloride, etc., where the electrode can be insulated by glass or lacquer, as well as silicon microelectronics, including tetrode or other multielectrode arrays or bundles, multichannel and ribbon devices. Typically, the electrodes can have relatively large tips with low resistance to detect activity from a number of neuronal elements within the neural system. Smaller tipped electrodes can be used for monitoring activity from single neurons or smaller populations. Activity can be measured from one or more electrodes, preferably two or more. In some cases, it may be desired to record from several regions of the neural system in order to characterize its activity. Recordings of intracellular, extracellular, or a combination thereof, can be analyzed separately, or together. The electrodes can be AC- or DC-coupled.

For certain purposes, iridium oxide type electrodes may be preferred since they are relatively nontoxic to cells, as well as being effective carriers of high current and charge densities. An activated iridium or iridium alloy wire can be used, or a metal substrate, such as noble metal (e.g., Au, Pt, or PtIr), ferrous steel alloy, stainless steel, tungsten, titanium, Si microprobe, etc., or other suitable substrate, can be coated with a film of iridium oxide to produce an effective electrode. Any suitable method to prepare the coating can be used, including, but not limited to, an activation process (e.g., Loeb et al., *J. Neuro. Sci. Methods*, 63:175–183, 1995; Anderson et al., *IEEE Trans. Biomed. Eng.*, 36:693–704, 1989) to form activated iridium oxide films (AIROFs), thermal decomposition (Robblea et al., *Mat. Res. Soc. Symp. Proc.*, 55:303–310, 1986) to form thermal iridium oxide films (TIROFs), reactive sputtering (15) to form sputtered iridium oxide films (SIROFs), electrodepositing (Kreider et al., *Sensors and Actuators*, B28:167–172, 1995) to form electrodeposited iridium oxide films (EIROFs), etc.

As described herein, it has been found that adaptive modulation of a neural system can be used to modify its neuronal activity. In preferred embodiments, this is achieved by characterizing the neuronal activity and then using a feedback algorithm to determine the field magnitude necessary to modulate its activity. Neuronal activity can be characterized by various measurements, depending upon the particular activity that is being assessed. When electrical activity is a determinant, then measurements can include, e.g., local field polarity and magnitude (e.g., −10 mV), burst activity, burst amplitude, burst frequency, power in a predetermined frequency band of activity, nonburst activity, single or small population firing rate, amplitude or phase of periodic activity, such as theta rhythm, root-mean-square (RMS), variance, etc. In general, any suitable measure of neuronal activity can be used as the feedback stimulus for the applied field. The feedback stimulus can also be determined by multiple measurements, e.g., electrical activity, limb motion, cochlear activity, etc.

In the examples, the neuronal activity, after appropriate filtering, was characterized by the RMS fluctuations of the measured signal, serving as the feedback stimulus. An electric field was subsequently applied in proportion to the RMS. Specifically, the instantaneous RMS activity (e.g., the last 0.25 sec of activity) was low pass filtered with a time constant $\tau$ to yield $A_\tau$. This value was compared with a threshold value, as determined by the long time average of the RMS (e.g., the last 30 seconds of activity). The magnitude of the applied field was then derived by calculating the difference between the $A_\tau$ and the threshold multiplied by a gain factor. Any suitable methods and/or algorithm for determining field strength and polarity can be used, e.g., linear and nonlinear proportional feedback, proportional—integral—differential feedback, etc.

The values for instantaneous activity and threshold can be selected empirically, e.g., based on the activity characteristics of the system and the neuronal activity that is to be controlled. The goal is to choose a time scale that distinguishes the activity of interest from the baseline activity of the system. When a timescale for the threshold (e.g., the last 30 seconds of total activity) and instantaneous (e.g., last 0.25 sec of total activity) activity determinations are selected, the difference between such values should permit detection of the onset of the activity of interest.

A gain factor can be chosen such that the output of the applied field is adequate to modulate the neuronal activity that is being monitored. It can be empirically derived, based on previous performance of the neural system and various considerations, including, e.g., magnitude of the onset of the event which is being assessed, magnitude of the applied field necessary to modulate the neural system, characteristics of the field electrodes, characteristics of the neural system environment, etc. In the experiments described herein, a gain was chosen such that a typical difference between $A_\tau$ and the threshold yielded a field in the range of order of 10 mV/mm. Successful control was achieved for the same experiment with gains differing by an order of magnitude indicating that the choice of gain was not critical.

The applied field can utilize the full feedback signal ("full-wave control"), or, it can be half-wave rectified. When half-wave rectification is used, a field is applied only when the instantaneous activity (or the calculated $A_\tau$) is above (or below) the threshold value. In the examples described below, a field was applied only when there was a positive difference between the instantaneous activity and the threshold. Thus, half-wave rectification indicates that the field is applied in only one direction. For full-wave control, a field is applied continuously when there is any difference between the instantaneous activity (or calculated $A_\tau$) and the threshold value. The outcome of half-wave rectification is the application of a field in only one direction, while full-wave control results in both negative and positive applied fields, depending upon the sign of the difference between instantaneous activity and threshold. As a result, full-wave control can involve the administration of both excitatory and suppressive signals, while half-wave rectification involves only one kind of signal, either excitatory or suppressive, depending upon the direction of the applied field. The experiments described below show that full-wave control was generally superior to half-wave rectification for seizure suppression, for reducing withdrawal seizures, and for obtaining a more regular baseline of neuronal activity.

Full-wave control may also be desirable to avoid substantial electrode and tissue polarization which occurs when half-wave rectification is used. In the latter case, the electrodes may need to repolarized between field applications, e.g., by applying bias currents to the electrodes.

In general, the duration and intensity of the applied field can be determined by the measured activity. If the purpose is to eliminate neuronal activity, then preferably a field potential, or current, is applied until the activity level is reduced below a threshold level. At this point, the field can be discontinued until activity is observed again. The applied field is preferably not a stationary field, such as the fields described in Gluckman et al., J. Neurophys., 76:4202–4205, 1996; U.S. Pat. No. 5,800,459. See, also, U.S. Pat. Nos. 5,797,965 and 5,522,863.

Activity can also be augmented, induced, or initiated. In the examples, reversing the field potential converted sporadic bursts into a full-blown seizure. In this case, the feedback stimulus is positive feedback, where the applied field is used to enhance activity, e.g., by producing depolarization toward threshold and/or recruiting more neurons into the activity. Here the sign of the gain factor is switched so that a negative field is applied when the RMS activity goes above threshold, forcing the network to become more excitable. The ability to create activity in vitro and in vivo is useful in variety of ways. It can be used to create animal models for epilepsy or electroconvulsive therapy (ECT) and for testing agents which modulate these brain behaviors for therapeutic, prophylactic, and research purposes. It can also be used to induce ECT in humans for therapeutic purposes.

In some instances, a neural system will exhibit ongoing neuronal activity, such as spike activity varying in amplitude and frequency. This information can be processed in any suitable way to serve as a threshold stimulus for the applied field. For instance, the activity in a certain frequency band can be of particular interest because it indicates that certain state of the neural system has been reached, such as epilepsy. It therefore may be desired to apply the electric field only when the system becomes epileptic. This can be accomplished by processing the measured neuronal activity, and applying the field when a predetermined threshold of activity is reached. For example, the long-term average of spontaneous or non-epileptic activity can be determined and used as the stimulus threshold, where no field is applied unless the long-term average, or a function of the average, is exceeded. A particular characteristic of neural activity can also be compared to a matched filter using a temporal, spectral, or wavelet filter, or a nonlinear filter, and its output compared with a threshold.

The methods and devices of the present invention are useful in any endeavor in which it is desired to modify the behavior of a neural system. In general, an applied field in accordance with the present invention can be utilized to modulate any neural activity, including, e.g., synchronized firing, oscillatory firing, pulsating activity, and any in-phase activity of a neural system. Because of such ability to augment or reduce neuronal activity of a neural system, the invention is useful for modulating many kinds of output which arise from neural systems, including motor, sensory, emotional, behavioral, etc.

For example, the methods and devices of the present invention are useful for treating brain diseases characterized by aberrant neuronal activity. Epilepsy, for instance, is a brain disorder characterized by recurrent seizures, affecting 1–2% of the population. In this disease, the pattern of neuronal discharge becomes transiently abnormal. In the examples, an in vitro slice preparation is utilized to illustrate how epilepsy can be treated in accordance with the present invention. When perfused in a high potassium concentration, these networks show a broad range of interictal-like and epileptiform activity, from network wide synchronous events to local and propagating events. Application of the adaptive electric field can be used to suppress the epileptiform activity, effectively treating and controlling the brain disorder.

A modulatory effect can be achieved analogously in situ. For instance, to treat a patient having epilepsy, a device can be utilized which simulates the pair of field electrodes used in the in vitro method. The field electrodes can be positioned in any arrangement which is effective to produce a modulatory field. They can be in contact with brain tissue or associated meninges, e.g., by inserting, through an occipital entrance hole, one, or more, long flat electrode strips that contacts the long axis of the hippocampus surface in the temporal horn of the lateral ventricle. A round electrode (e.g., a single depth electrode with one or more suitable high current contacts) can also be utilized, e.g., by placing it within the long axis of the hippocampus in order to produce a radial electric field. Electrodes can also be external to the brain, e.g., on the scalp. The electrode strip preferably produces an effective electric field. Useful electrode strips include non-polarizing biocompatible electrodes embedded in silastic sheets with sealed electrode-lead connections, similar to those used for cochlear implants, e.g., a Clarion Cochlear Implant, comprising iridium oxide electrodes sealed within a curved silastic silicone elastomer sheath. In another embodiment, a sheet comprising multiple electrodes can be placed over the neocortex in the subdural, subarachnoid, or epidural spaces, or within the sulci of the brain. Thin electrodes can also be inserted into brain tissue. In general, any types or combinations of electrodes, such as those mentioned above, can be used.

In addition to epilepsy, any brain disorder that displays abnormal activity, such as oscillatory or pulsating activity, can be treated analogously. Such diseases, include, schizophrenia, depression (unipolar or bipolar), Parkinson's disease, anxiety, obsessivecompulsive disorder (OCD), etc., where the electric field is applied to the particular brain region exhibiting the abnormal activity, e.g., cortex, hippocampus, thalamus, etc. Parkinson's disease is characterized by decreased activity in cells that produce dopamine. Patients with the disease experience tremors, rigidity, and difficulty in movement. Patients with Parkinson's disease can be treated by applying an electric field in an amount effective to ameliorate one or more symptoms of the disease. Preferably, the applied field is sub-threshold. The field electrodes can be placed in any suitable region of the brain, such as the thalamus or basal ganglia. The electrodes can be of the same in situ type described above for treating epilepsy. The amount of applied field can be changed in response to an electrical activity in the brain, or in response to a manifestation of such electrical activity. For instance, the field can be applied until one or more symptoms are eliminated, such as tremors or difficulty in initiating movement. In such case, the field can be operated manually by the patient, or the behavior can be monitored automatically by feedback sensors either within the brain or placed strategically along the body to sense the behavioral output.

A method of the present invention also relates to restoring or repairing a brain function. These functions include, e.g., sensory functions, such as vision, hearing, smell, touch, and taste, motor activity and function, somatic activity and function, etc. For instance, the method can be useful to treat a condition where an animal (e.g., a human) has lost its vision due to a peripheral defect, such as the loss of an eye, but the visual cortex is largely intact. The present invention can be used to restore vision by creating patterned activity in the brain using an applied field. For example, devices can be used to capture images (e.g., light intensity, wavelength, etc.), process the information, and use the information as a feedback stimulus to the visual cortex, or a subservient pathway, modulating the on-going cortical activity analogously to how epileptic activity was induced from non-epileptic activity as described above and below. Similar strategies can be applied to restoring other lost functions, e.g., hearing or touch to the auditory or somatosensory cortex, respectively.

The present invention also relates to a field-producing device for modifying the neuronal activity of a neural system comprising neurons. Such device is not a voltage-clamp device, or a patch-clamp, as used to clamp the activity of single neurons, or parts thereof. A field-producing device can comprise one or more of the following components: (a) field electrode means for applying an external electric field to a neural system; (b) field application electronic means for generating an external field to a neural system, which is operably connected to (a) field electrode means; (c) measuring means for monitoring the neural activity of the neural system; (d) measurement electronics means for recording neural activity, which is operably connected to (d) measuring electronic means; (e) feedback controller means for determining the amount of external field to apply to the neural system, which is operably connected to (b) field application means and (c) measuring means; (f) sensing means for detecting the external field produced by the field electrode means; (g) sensing electronic means for recording the field produced by the field electrode means, which is operably connected to (f) sensing electrode means and (b) field application means. The device can be used for in vitro applications, or as as in vivo prosthetic devices for treating brain disorders, such as epilepsy and Parkinson's disease, and restoring brain function. In the latter case, the (f) sensing electrodes and (g) electronics are optional.

FIG. 1 illustrates an in vitro field-producing device. In this example, the (b) field application electronic means and (g) sensing electronic means are bundled together, along with an isolation stage. The (d) measuring electronic means is an amplifier of the type typically used to record extracellular and intracellular neuronal activity. The (e) feedback controller means in the example is a computer loaded with the appropriate software for taking data in from the recording electronics and outputting a signal, derived from feedback algorithm, to the field electronics. FIG. 1 also contains a computer ("user interface 7) for recording and displaying information from the various components of the device The device preferably is for applying a sub-threshold field. It can further comprise a power source for generating the applied field (e.g., a direct or inductive source); external feedback sensors for detecting behavioral output, etc.

For in vivo applications, various methods can be used to place the electrodes the in target tissue, including, visually, stereotactically, endoscopically, ultrasonically, x-rays (such as CT scan), nuclear magnetic resonance, electrical activity, etc.

In addition to identifying characteristics to be used in calculating a feedback stimulus, an additional parameter that can be varied is the choice of the activity that is being measured. Thus, for instance, the feedback stimulus activity can be measured intracellularly from one or more neurons, or extracellularly, capturing field potential from single neurons or a neuronal population. Additionally, the feedback stimulus can be remote or external to the neural system. Thus, the feedback stimulus can be recorded at the site of field application (e.g., using measuring electrodes placed in the tissue), at site remote from the field application, or using a behavioral feedback stimulus, such as movement of a limb when motor activity is modulated, or the ability to experience a sensation when sensory activity is modulated.

The present invention also relates to methods of identifying pharmacological agents which modulate the neuronal activity of a neural system comprising neurons, comprising one or more of the following steps in any order, e.g., measuring the neuronal activity of a neural system; applying an oriented electric field to said neural system effective to modify the neuronal activity of the neural system, wherein the magnitude and polarity of said applied electric field is changed in response to the measured neuronal activity; and administering an agent which modulates the neuronal activity of the neural system. Such a method is especially useful for identifying agents that can be used therapeutically and/or prophylactically in brain disease. Any agent can be administered to the neural system, including, e.g., neurotransmitter agonists and antagonists (such as, serotonin, dopamine, GABA, glutamate), sympathomimetics, cholinergics, adrenergics, muscarinics, antispasmodics, hormones, peptides, genes (sense and antisense, including genetic therapy), metabolites, cells (e.g., where neural grafting is being used as a modulatory therapy), sedatives, hypnotics, anti-epileptics (e.g., acetazolamide, amphetamine, carbamazepine, chloropromazine, clorazepate, dextroamphetamine, dimenhydrinate, ephedrine, divalproex, ethosuximide, magnesium sulfate, mephenytoin, metharbital, methsuximide, oxazepam, paraldehyde, pamethadione, phenacemide, phenobarbital, phensuximide, phenytoin, primidone, trimethadione, valproate, etc.), hormones, peptides, etc.

In an in vitro method and device of the present invention, a slice of rat brain tissue obtained from the hippocampus of the temporal lobe is perfused with an oxygenated physiological perfusate fluid ("ACSF" or artificial cerebrospinal fluid) in an interface-type perfusion chamber (e.g., Hass-style) comprising an inlet 9 and outlet 10 for continuously replacing the perfusate. A heated oxygen/carbon dioxide gas (95% oxygen, 5% carbon dioxide at 35° C.) is provided through inlet 11. The top of the chamber can be open, or covered.

The anatomy of the brain tissue includes layers of pyramidal neurons of the Coruu Ammonis (CA) regions. In order to induce seizures, the ACSF perfusate is replaced through the inlet 9 with a high potassium solution, comprising 8.5 mM potassium and 141 mM chloride. The elevated potassium produces epileptic activity characterized by events in the form of spontaneous burst firings and seizure-like events within the two regions (CA3 and CA1 respectively) at opposite ends of the Cornu Ammonis. Seizure-like activity can also be produced by other treatments, including, penicillin, low magnesium, kainic acid lesions, or any one of the epileptogenic compounds. Additionally, naturally-occurring and induced mutants which result in aberrant brain activity, including mutants produced by genetic-engineering, e.g., in channel genes and receptor genes, can be used as a source of brain tissue.

The brain tissue slice labeled by reference numeral 1 in FIG. 1 is supported on a nylon mesh 2 submerged in artificial cerebrospinal fluid the perfusate within a chamber formed by an annular wall 3. A pair of parallel spaced Ag—AgCl field electrode plates 4 (F1, F2) are placed on the floor of the chamber, positioned in such a manner to produce an electric field parallel to the soma-dendritic axis. The field electrodes 4 are spaced apart from each other, for example by 1.8 cm. An electric field is established between the electrodes 4 in the perfusion chamber within which the tissue slice 1 is submerged in the perfusate fluid. A pair of ground electrodes 10 (G) are positioned on the floor of the chamber. A pair of Ag—AgCl sensing electrodes 5 (S1, S2), placed 12 mm apart, are shown in FIG. 1 for sensing the field produced by the electrodes 4 and to feedback control the field in the chamber. Micropipette measuring electrodes 12 (above the chamber) are used to measure neuronal activity extracellularly. The electronics are set up so that the potential between S1 and S2 is equal to a gain (of 1 or 0.1) times the program potential (from the computer or a waveform generator).

The measuring electrodes 12 are adjacent to the pyramidal cell layer of the brain tissue slice 1 at a position along a field isopotential to minimize recording artifact by means of differential amplification. Such positional arrangement of the electrodes 12 allows for continuous recording of neuronal activity in the brain tissue slice 1 despite relatively substantial changes in the electric field established between the electrodes 4.

The potential measured through the measuring electrodes 12 are filtered through the recording amplifier 6 and directed to the user interface for monitoring and parameter control 7 and the feedback controller 8. The monitoring and parameter control 7 can accept input from the recording electrode 6 and the feedback controller 8, and display and record such input. Based on the measured activity from the recording electrodes 12, an electric field is externally imposed on the brain tissue slice 1 by applying a potential difference to the electrodes 4 through the field application electronics 9. The amount of generated field is determined by the feedback controller 8 which accepts information from the recording (measuring) electrode electronics 6 about the activity of the neural system, and using a selected algorithm (either as software, hardware, or a combination), generates a signal to the field electronics 9. This signal to the field electronics 9 results in the application of a field by the field electrode means 4. The field application electronics 9 comprises an amplifier circuit through a 4-probe feedback technique which applies a potential (or current) between the field electrodes 4 in order to set the field between the sensing electrodes 5 equal to the amplifier's program voltage times a gain (gain=1 or 0.1). Built into this circuit is a layer of ground isolation stage that allow its potentials to float from those of the recording system.

The electronics used to control the field can comprise an input stage A, a standard summing amplifier with a switchable gain of either 1.0 or 0.1 and a low pass frequency of 10 kHz. The output of A is sent both to a monitoring stage B, and to an isolated output stage C. The monitoring stage B can be composed of a unity gain non-inverting amplifier which acts as a buffer to a monitoring channel for recording the summed input. The output stage C can be a circuit utilizing the Analog Devices AMP01 instrumentation amplifier and a OP37 op-amp which provides the feedback stabilized field via the Ag—AgCl electrode plates in a chamber D. This stage can be separately powered by rechargeable batteries in order to isolate this circuit from measurement ground. Unity gain buffers (e.g., from an AD712 op-amp) used to minimize the current through sensing plates S1 and S2.

EXAMPLES

Materials and Methods

Tissue preparations. Sprague-Dawley rats weighing 125–150 gm were anesthetized with diethyl-ether and decapitated in a accordance with a George Mason University Animal Use Review Board approved protocol. Hippocampal slices 400 m thick were prepared with a tissue chopper, cut either transversely or longitudinally with respect to the long axis of the hippocampus, and placed in an interface type perfusion chamber at 35° C. After 90 min of incubation in normal artificial cerebrospinal fluid (ACSF: 155 mM $Na^+$, 136 mM $Cl^-$, 3.5 mM $K^+$, 1.2 mM $Ca^{2+}$, 1.2 mM $Mg^{2+}$, 1.25 mM $PO_4^{2-}$, 24 mM $HCO_3^-$, 1.2 mM $SO_4^{2-}$, and 10 mM dextrose), the perfusate was replaced with elevated potassium ACSF (8.5 mM [$K^+$] and 141 mM [$Cl^-$]) and the slices were allowed another 30 min incubation time. In some experiments, transverse slices were further cut so as to isolate just the CA1 region, and then allowed to incubate longer until seizures were observed.

Experimental apparatus and electronics. A schematic of the experimental system is shown in FIG. 1. A uniform electric field was introduced by passing current between a pair of large Ag—AgCl plates embedded in the chamber floor relatively far from the slice (17 mm plate separation). A 4 electrode technique was employed, where a separate pair of electrodes was used to sense the field in addition to the pair of field producing electrodes (Cole, 1972). This eliminated effects from the slow polarization known to occur even in "nonpolarizing" Ag—AgCl electrodes. Field application electronics were used that control the current between the field plates such that the potential difference between the sensing electronics equals an input voltage signal and such that the potential of the plates float with respect to signal ground (defined by a pair of Ag—AgCl plates near the chamber midline). The input voltage signal to the field electronics was computer-generated, and low pass filtered (<30 kHz) in order to eliminate artifacts from the digital to analog conversion.

Electrophysiological recordings: Synchronous neuronal population activity was monitored by measuring the extracellular potential in the cell body layer of the CA1 region. Extracellular recordings were made with paired saline filled micropipette electrodes (1–4 M ) and a differential DC coupled amplifier (Grass Model P16). In order to produce a feedback system, measurement of neuronal activity must be performed simultaneously with the applied field. Two approaches to minimizing artifact from the field in the recordings were used. First, the micropipette electrodes were aligned as close as possible to an isopotential of the applied field. Alignment was achieved by applying a sinusoidal field and adjusting the position of the reference electrode so as to minimize the field artifact. This allowed us to measure neuronal activity in the presence of relatively large (50–100 mV/mm) fields with high resolution and without saturating the recording amplifiers. Second, since some stimulus artifact persists in our measurements, we additionally restricted the frequency content of the applied field to be distinct from that of the measured activity of primary interest.

Feedback algorithm. For feedback purposes we characterized the neuronal activity associated with seizures as the RMS of the recorded activity measured within a frequency band of 100–500 Hz, averaged over a time which varied from 0.1–1.5 s. The applied field was proportional to the positive difference between this RMS activity and a threshold value. The threshold was set by an average (~30–3000 s) of the measured RMS power. The frequency content of the applied field was restricted to less than 10 Hertz. For practical purposes, a maximal (saturation) field amplitude was enforced. In some applications, the output field was half-wave rectified (i.e. when the RMS was below threshold, no field was applied). Both the gain and the threshold were set empirically. In general, optimal control was found with a moderate gain which could be estimated by ~(50 millivolts/mm)/(peak recorded power of a seizure).

Field strengths are presented in units of mV/mm, with positive field correspondingly aligned with the primary dendrite-soma axis to produce a suppressive effect, as illustrated at the bottom of FIG. 1. Gains are presented in arbitrary units, with positive gain corresponding to negative feedback mode.

Analysis Methods

Seizure-like events in these slices are characterized from extracellular field potential recordings by an extended burst of high frequency (100–350 Hz) activity accompanied by a relatively large (0.2–5 mV) low frequency (0.01–1 Hz) negative potential shift which typically lasts many seconds. Three methods were used to characterize neuronal activity from the field potential recordings. First, events were detected from the high frequency activity in the field potentials. The RMS power in the frequency band 100–300 Hz was calculated from the field potential recordings with a time constant of 0.1–0.5 s, then analyzed with a simple threshold crossing event detection scheme. These "RMS events" were then characterized by their average and maximum power and duration. Second, events were detected from the low frequency deflection in the field potentials. The field potential recordings were low-pass filtered with a cutoff at 10 Hz, and threshold crossing again applied. These "DC events" were characterized by their average and maximum potential shift, as well as duration. We note that because these analyses are based on distinct or separate frequency bands, they are independent measures. Finally, spectral methods were used to characterize average frequency content of the neuronal activity during different types of stimuli.

Prior to each of the above-mentioned analyses, the linear component of the stimulus artifact was calculated from the cross-correlation coefficient between the field-potential recordings and the stimulus. The stimulus artifact accounted for less than 5% of the RMS deviations in the field-potential recordings.

Results

Electric fields are known to modulate neuronal activity and even transiently suppress seizure-like activity (Gluckman, et. al., 1996a). Our objective in this work was to demonstrate that, when applied in a feedback fashion, that control of seizure-like network behavior could be achieved for extended periods of time.

Field Characteristics

Figure 2:
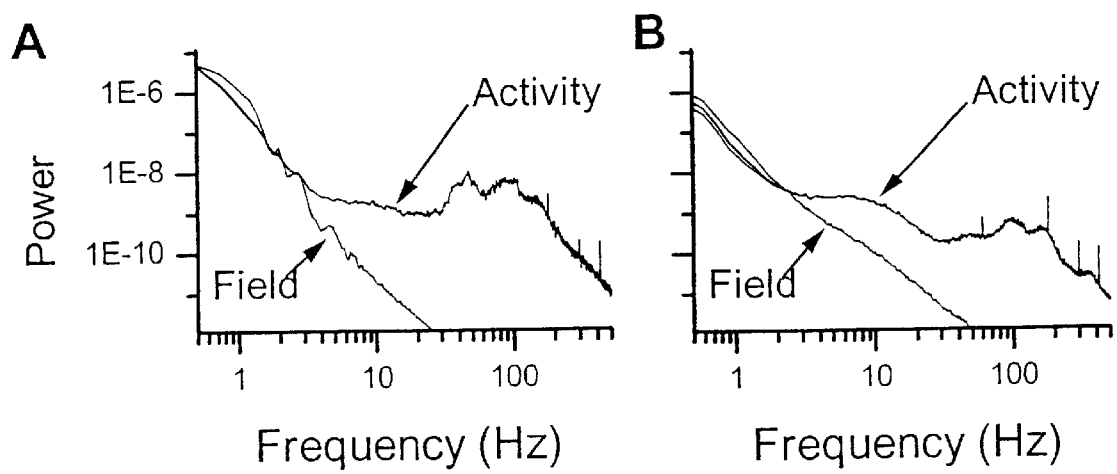
FIG. 2. Power spectral density (PSD) for recorded activity and applied field stimulus in the case for which the stimulus was a low frequency random signal (A) and for which the stimulus was a typical feedback control signal (B). For display purposes, the stimulus PSD was vertically scaled such that its amplitude matched that of the recorded activity PSD at low frequencies. In both cases, the stimulus PSD falls off quickly ($\sim f^2$) for frequencies, f above about 4 Hz, in contrast to the neuronal activity PSDs, which have significant spectral power up to approximately 350 Hz. Also shown are the PSDs of the recorded neuronal activity after removal of an estimate of the stimulus artifact. These signals are indistinguishable from the original recording for frequencies above ~2 Hz. In (B) the raw signal lies slightly below the processed signal for low frequencies. These results indicate that the applied field during control is not simply masking the neuronal activity in the recording process during control. The stimulus artifact accounts for less than 5% of the RMS recorded signal amplitude.

Critical to performing these experiments was our ability to record neuronal activity independent of the applied time-varying electric field stimulus with minimal field stimulation artifact in the recording. We achieve this with the use of DC differential recordings from paired electrodes aligned to be nearly on the same isopotential of the applied field. We further restricted our applied field to have frequency content in a band distinct from that of the signal in which we were interested. This distinction is illustrated in FIG. 2. Power spectra for recorded activity and applied field are shown for both the case where the applied field is noise (2A) and the case where the field is a typical feedback signal (2B). In addition, we have post-processed our recording to eliminate the residual artifact, which typically constitutes less than 5% of the RMS field-potential variations. The power spectra for the processed signals is also shown in these plots, and is indistinguishable from the unprocessed signals except at low (<3 Hz) frequencies. These results indicate that the applied field during control is not simply masking the neuronal activity in the recording process during control. Since the applied field was restricted to have frequency content below 10 Hz, it only changes the character of the field potential recordings at the lowest frequencies.

Overview of Control Phenomena

There is a characteristic low frequency negative potential shift of the tissue associated with these seizure-like events in vitro (Traynelis and Dingledine, 1988) that is quite similar to the slow low frequency potential shifts observed during in vitro seizures (Wadman et al., 1992). Typical seizure-like events in these slices exhibited durations of order 5–25 seconds and inter-event intervals of order 40 seconds, and low frequency (0.01–1 Hz) potential shifts of order 0.2–5 mV. Recording to recording variations in the morphology and amplitude of DC deflection can be attributed to the details of the measurement electrode location with respect to both the origin of the seizure and to the position of the reference electrode.

Figure 3:
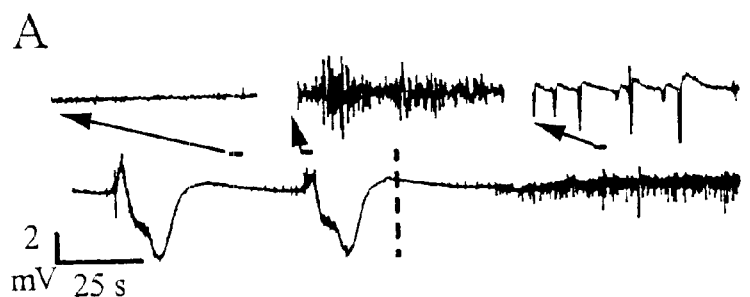
FIG. 3. Adaptive control of seizure activity using applied electric fields. In each panel, the main trace is the raw extracellular potential recording. Insets are tracings of activity, filtered to illustrate the high frequency activity, shown at expanded scales. In each case, a dashed line is used to demarcate when control is turned on. A,B: Examples of seizure suppression from separate experiments using electric fields applied as a negative feedback parameter. Electrographic seizures are observed as an increase in high frequency activity atop large low-frequency deflections (Traynelis and Dingledine, 1988). In B, seizures occur interspersed among frequent short network bursts (Rutecki et al., 1985). C: Example of seizure induction achieved using positive feedback.
Figure 3:
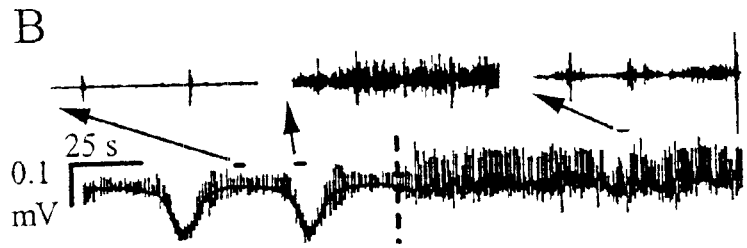
Figure 3:
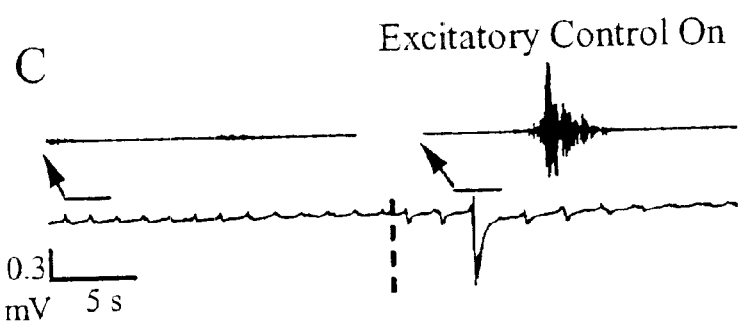

Seizure Suppression: In FIGS. 3A and 3B we show examples that illustrate how an electric field can be used to adaptively suppress seizure-like activity within the CA1. Suppression is achieved by using negative feedback. In both cases the high frequency activity, towards which the suppression algorithm is directed, is significantly attenuated. The DC shift was completely eliminated (3A) during suppression for some slices, while it was partially retained (3B) for others. During control, some non-zero level of network activity is still observed from the field potentials (third inset in each). We have documented successful suppression in 20 of 30 seizing slices with which we applied adaptive control.

Control can often be maintained for prolonged periods of time. To date, the longest we have maintained control is 16 minutes in a slice otherwise exhibiting seizures approximately every 40 seconds. Since the amplitude, duration and interval between of the events slowly change over the course of an hour (see FIG. 4), 16 minutes is near the limit for reliable suppression testing in this system.

Seizure Enhancement: Positive feedback, set by changing the sign on the gain which reverses the applied field polarity, can be used to either enhance seizures or even create seizures where none were observed beforehand. In FIG. 3C, we show an example of the characteristic population burst-firing events seen in high [K$^+$] hippocampal slices (Rutecki et al., 1985) in the uncontrolled state. With positive feedback control, the adaptively applied field now enhances the brief network bursts into large seizure-like events with the substantial low frequency potential shifts characteristic of seizures. We have documented seizure generation in all 4 non-sizing slices with which we applied positive feedback control.

Comparison of Parameters: a Single Experiment

Figure 4:
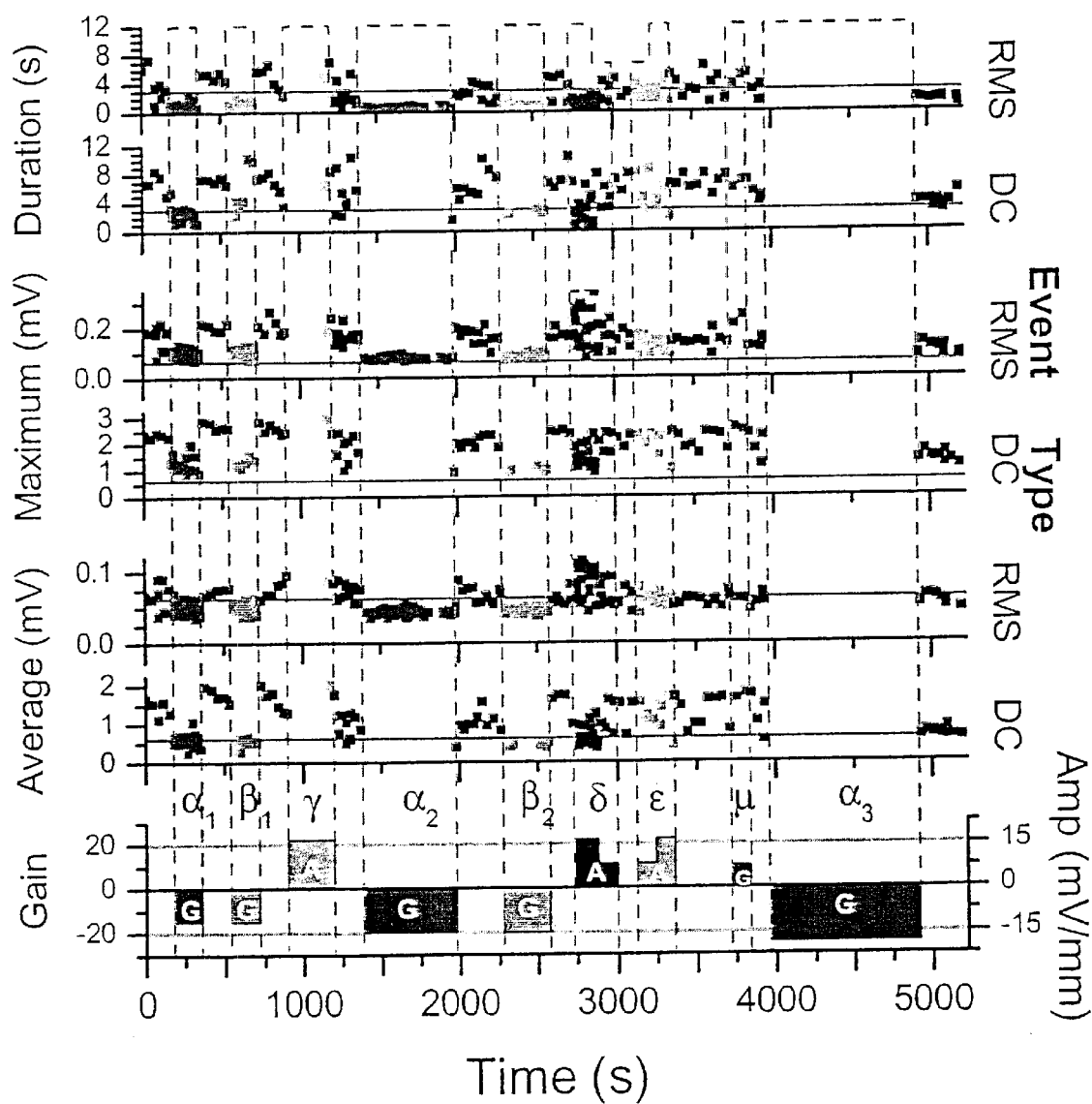
FIG. 4. Event detection results for a single 90 minute recording, with different electric field stimuli applied. The lower trace indicates feedback gain (G, left axis) or amplitude (A, right axis) of the applied stimulus. Greek letters indicate type of stimulus: baseline (no letter); full-wave feedback control ($\alpha$); half-wave rectified feedback control ($\beta$); constant amplitude suppressive field ($\gamma$); low frequency noise ($\delta$); suppressive half-wave rectified low frequency noise ($\epsilon$); positive feedback control ($\mu$). Two types of event detection were used to identify synchronous neuronal activity from the recorded field potentials. "RMS events" were detected from variations in the RMS power in the frequency band 100–350 Hz. "DC events" were detected by threshold detection after low pass filtering the recordings at 10 Hz. The character of both types of events, as quantified by their average and maximal amplitudes as well as their duration, was visibly changed from baseline when control was applied. No events of either type were observed during the final and longest (16 minutes) application ($\alpha_3$) of full-wave control.

Detailed event extraction results for a 90-minute recording from a single experiment is shown in FIG. 4. In this experiment, we compared the application of negative feedback both with and without half-wave rectification of the applied field at various gains, application of a constant amplitude suppressive field and random waveform fields, as well as positive feedback control. From this experiment, we extracted events both from the RMS power in the frequency band 100<f<350 Hz, which we term "RMS events," and events from the low frequency (f<10 Hz) potential shifts, which we term "DC events."

The type of stimulus applied is indicated in the lower trace, where the height of the blocks indicate either the gain (G, left axis) used in the proportional feedback routine, or the amplitude (A, right axis) of the waveform applied. The Greek letters indicate the type of stimulus applied, as indicated in the figure caption. Baseline recordings of 1–4 minutes were made between stimuli. In the upper plots are shown the duration, maximum and average deflections (DC or RMS power) of all events extracted either from the RMS power ("RMS events", upper trace for each pair) or low frequency deflections ("DC events") as a function of time. Values for all extracted events are plotted. For the maximum and average deflections, the horizontal lines correspond to the trigger threshold for defining an event. As expected, the maximum deflections are always greater than or equal to the trigger threshold. In contrast, the average deflection need not be larger than the trigger threshold. Therefore, the trigger threshold provides a logical dividing line between large and small events in the average deflection plots. In the duration plots, a horizontal line at 3 seconds is plotted as a rough threshold for distinguishing seizure-like episodes from smaller burst-like events.

Feedback Suppression: Negative (i.e. suppressive) feedback, indicated by a negative gain, was applied with both full-wave ($\alpha$) and half-wave ($\beta$) rectification. Even at the smallest gain used ($\alpha_1$, $\beta_1$), all six types of event characteristics are distinct from the baseline activity (black) for both detection schemes. At the intermediate gain used, no DC events were observed during the non-rectified control ($\alpha_2$), while only short, low power RMS events were observed. For half-wave rectified control at comparable gain ($\beta_2$), short, small events were observed from both the DC and the RMS event extraction. At the highest gain used for non-rectified control ($\alpha_3$, starting at time 3960 s), no DC or RMS events were detected throughout the 16 minutes of control application.

Figure 5:
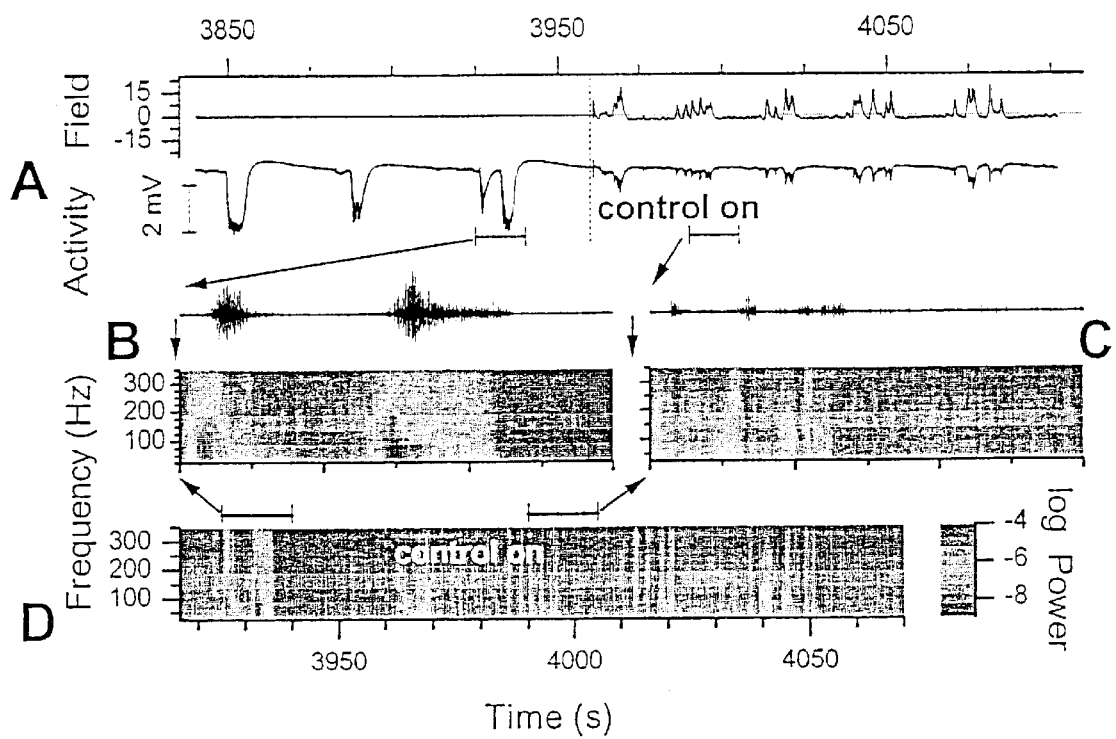
FIG. 5. Traces and spectrograms of activity with and without control for same experiment as FIG. 4. (A) Activity (lower trace) and applied field (upper trace) from the final application of full-wave control ($\alpha_3$) from FIG. 4 and the baseline preceding it. (B,C) A 15 second long trace and spectrogram of a seizure-like event (B) and of activity during control (C) from A. The upper traces in B and C are the activity, high-pass filtered at 100 Hz. The spectrograms (B, C, D) are calculated in overlapping vertical frequency bins 50 Hz tall from 25–350 Hz, and in overlapping horizontal time windows 0.05 s wide. (D) Spectrogram for longer period illustrating contrast between baseline and controlled activity.

Examples of activity for this experiment with and without control are shown in FIG. 5. The upper pair of traces (A) correspond to the measured field potential (lower) and applied field (upper) starting 2 minutes prior to the last application of non-rectified control ($\alpha_3$). The baseline activity, without control, is characterized by large seizure-like events that start with a burst of high frequency activity, which are accompanied by a large low frequency potential shifts. Details of one of these events are shown in the trace of B at an expanded scale (15 s), high-pass filtered at 100 Hz, along with a spectrogram of the activity covering frequencies from 25–350 Hz. The power associated with these seizures can be observed in the spectrogram to start at high frequencies (near 120 Hz) and progress toward lower frequencies, a characteristic known as a 'spectral chirp'. Similar spectral chirps have been observed to be spectral signature of human seizures (Schiff, et. al., 2000). The neuronal activity following the seizure-like events in our experiments, as measured by the RMS power, is depressed across all frequencies.

Expanded views for recorded neuronal activity during control are shown in FIG. 5C with the same scales as B. Although the RMS power fluctuates during control (C), it never approaches the level observed in baseline (B). Note that the color scale is logarithmic. This behavior continues throughout the 16-minute of this control application (FIG. 4, $\alpha_3$), where the fluctuation are never large enough to trigger the RMS event detection. A spectrogram corresponding to a longer period (150 s) crossing from baseline to control is shown in D. Throughout the control period, the RMS power activity lacks both the characteristic highs and lows observed during non-controlled activity. We note that this power reduction/stabilization occurs across all frequencies displayed (25–350 Hz), whereas the applied field was constrained to have frequency content only below ~10 Hz. The RMS amplitude of the applied field averaged over the full control period was ~4.8 mV/mm, and typically much smaller than the allowed maximum of 17.5 mV/mm.

Figure 6:
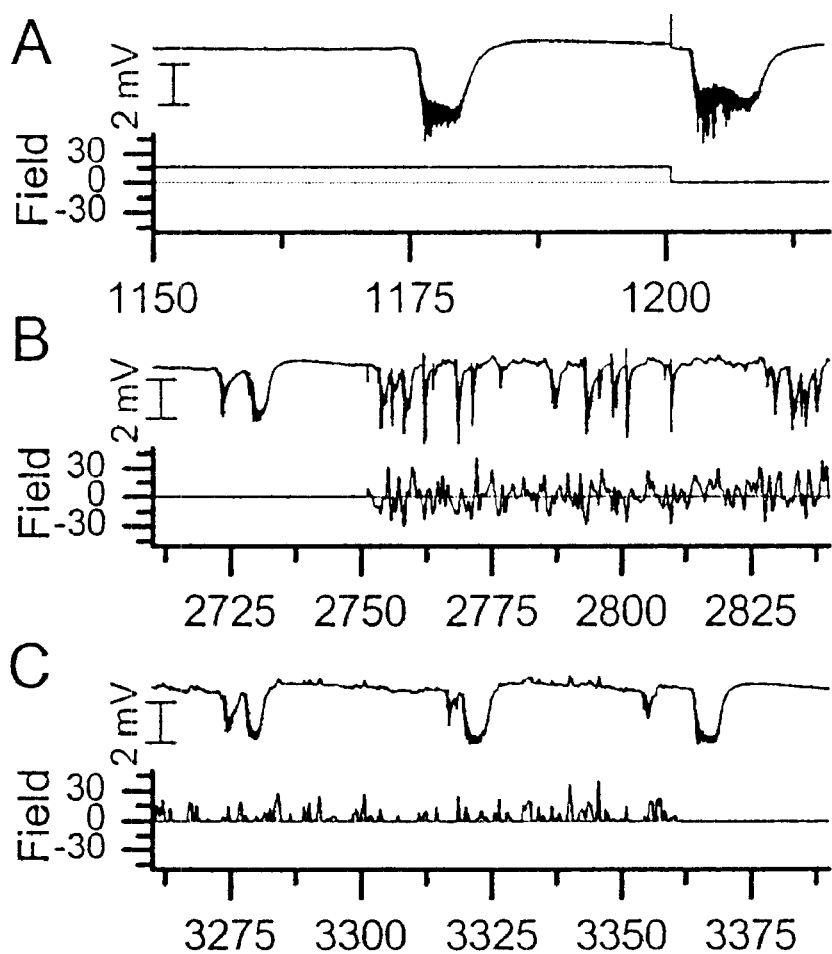
FIG. 6. Examples of activity during non-feedback electric field stimulus for the same recording as FIG. 4. For each set, the upper trace is of the recorded activity, while the applied field is shown in the lower trace. (A) Application of constant-amplitude (DC) suppressive field ($4\gamma$). (B) Application of full-wave low frequency noise field ($4\delta$). (C) Application of half-wave rectified low frequency noise field ($4\epsilon$). In each case, large neuronal events are observed, though the full-wave noise field did have the effect of breaking up the seizure-like events into shorter durations.

Suppression with constant field: A relatively large suppressive constant (DC) field (16.7 mV/mm) was applied starting at time 900 s (FIG. 4, γ). As was observed in earlier work (Gluckman, et. al. 1996a), this had the effect of suppressing the large seizure like events observed with no field. However, the effect had limited duration, as a large seizure-like event was observed 276 seconds after initiation of the field, as shown in FIG. 6A. This is in contrast to the 600 s period of control initiated at time t=1400 s, during which no large events were observed (FIG. 4, $\alpha_2$).

Stimulation with low frequency noise: One hypothesis might be that any low frequency field might elicit a similar suppressive effect on the neuronal activity. We have tested various non-adaptive periodic and random signals. Although such signals do tend to modulate neuronal activity, we have observed little effective suppressive effect on seizures. Examples of a random signals were used in the experiment of FIG. 4. Application δ corresponds to a full-wave (suppressive and enhancing) random field, while ε corresponds to a half-wave rectified (only suppressive) random field. Each was restricted to have frequency content below 1 Hz. Examples of activity from each of these applications are shown in FIGS. 6B,C. The full-wave random field (6B) did have the overall effect of breaking up the seizures in time and decreasing their duration as measured by the RMS event extraction (Top of 4). However, the maximum amplitude of those events as measured in the RMS was typically larger than baseline, and comparable findings were reflected in the low frequency deflections (DC events). The half-wave rectified field (6C) had little effect at either amplitude used.

Positive Feedback control: We applied a positive feedback for a short duration during this experiment. During this time, two events were observed, both of which were relatively large as measured from the average and maximum deflection for both RMS and DC detection methods (FIG. 4, μ), as compared to the baseline events nearby in time.

Figure 7:
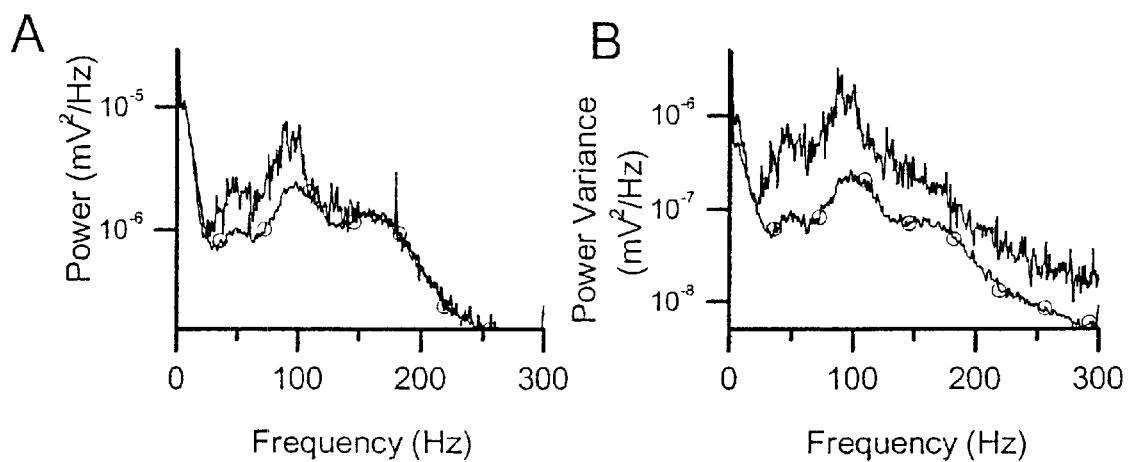
FIG. 7. Comparison of power spectral density (PSD) of recorded activity during control (lines with symbols) as compared to baseline (lines without symbols). The control corresponds to the final control application in FIG. 4, and the baseline corresponds to the final baseline application. PSDs were calculated in overlapping 1.64 s ($2^{14}$ point) windows. The power averaged over the windows is shown in A, while the window to window variance of power is shown in B. For both measures, the controlled activity falls well below that of the baseline activity.

Statistics using power spectra: The character of the neural activity during control can be further quantified from the average power spectra. Spectra from the last control application in FIG. 4 and the baseline recording following it are shown in FIG. 7A. These averages were calculated by averaging the spectra of 1.63 s ($2^{14}$=16384 points, recorded at 10 kHz) half-overlapping windows. The standard deviation of power as a function of frequency, which represents window to window power variations, is shown in 7B. For both of these measures, the curve for the controlled activity (line with symbols) lies well below that of the baseline activity.

Figure 8:
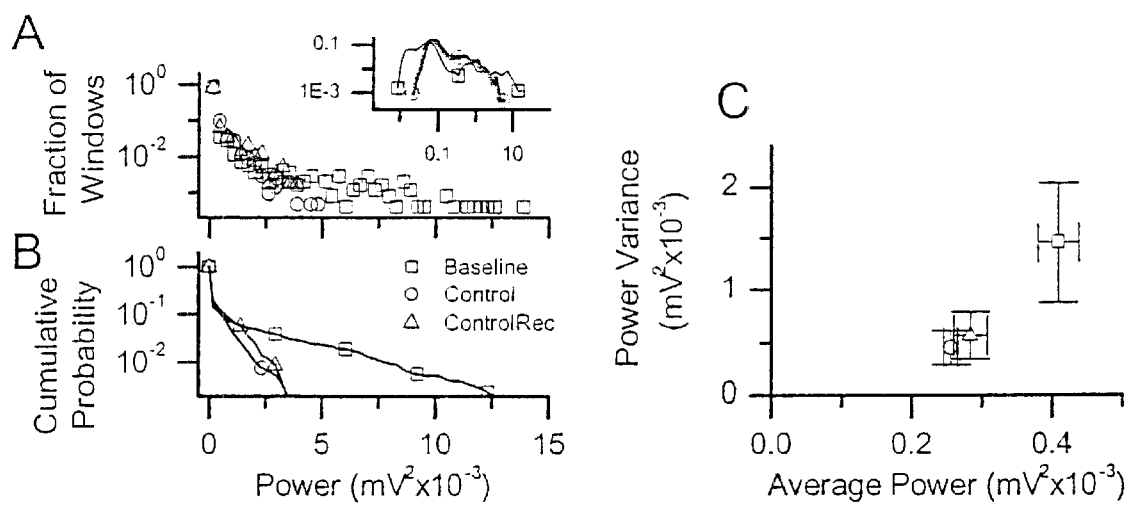
FIG. 8. Statistics of the RMS power of recorded activity in the frequency band 100–350 Hz, calculated in 1.64 s windows, for baseline (squares), full-wave control (circles) and half-wave rectified control (triangles). Statistics correspond to all applications independent of gain for the recording of FIG. 4. The normalized histogram and cumulative probability are shown in (A) and (B). It is clear that the baseline activity has many windows with much higher power than either type of control. These windows correspond to the first phase of the seizures. The inset in A is the normalized histogram of power calculated with logarithmically spaced bins (power, abscissa; frequency, ordinate) for baseline (boxes) and full-wave control (circles). From this plot, it is observed that deviations to both high and low power are eliminated during full-wave control. The windows with extremely low power correspond to the latter phase of the seizures and the recovery times following them. The power variance vs. average power is plotted in (C) for these three conditions. The two types of control are statistically well distinguished from that of the baseline activity.

Although our objective was to suppress the seizure-like events, the control law we used (the algorithm) was designed to limit the RMS power of recorded neural activity in a frequency band from 100–500 Hz. We can therefore quantify the success of this controller by investigating the statistics of the RMS power integrated over the frequency band 100–350 Hz, again for overlapping 1.63 s windows. The power above about 250 Hz is negligible (FIG. 5). This measure should be independent of stimulus artifact, since the power associated with the stimulus is confined to frequencies below 10 Hz (FIG. 2). Normalized histograms of this integrated power are shown in FIG. 8A, for the baseline recordings (squares), during full-wave feedback control (α, circles) and half-wave rectified control (β, triangles) for the whole recording of FIG. 4. The distributions for all three conditions are populated primarily with windows of low power. The windows with high power are of great interest, since we associate high power in this frequency band with the first portion of the seizure-like events. To highlight the tails of these distributions, we compute the cumulative probability, shown in FIG. 8B. This distribution, C(p), can be understood to be the fraction of windows with power greater than p. From it, we observe that the maximum power observed during baseline is roughly 4 times higher than observed during control. In addition, roughly 3% of the windows during baseline activity have higher power than the maximum observed during either type of control.

The high-frequency burst of activity in the uncontrolled seizure-like events is usually followed by a quiet, refractory-like period. During full-wave control, the objective of the control algorithm was to maintain a target level of activity by either suppressing or exciting the network. In order to further illustrate the controller's efficacy, we show in the inset of 8A the normalized histogram of power for baseline (squares) and full-wave feedback (circles, thick line) control computed with logarithmic bins (power, abscissa; frequency, ordinate). From this graph, it is clear that such excursions to low power are also curtailed during full-wave control. Half-wave rectified control (not shown) also decreased these excursions, but to a lesser extent.

The window-to-window variance of the integrated power is plotted vs. the average power in FIG. 8C for each of these conditions (baseline, control, and rectified control). We use the variance as a measure of the width of the distribution. The baseline activity is clearly differentiated statistically from both types of controlled activity using either the mean or variance as measures.

Release Phenomena

Figure 9:
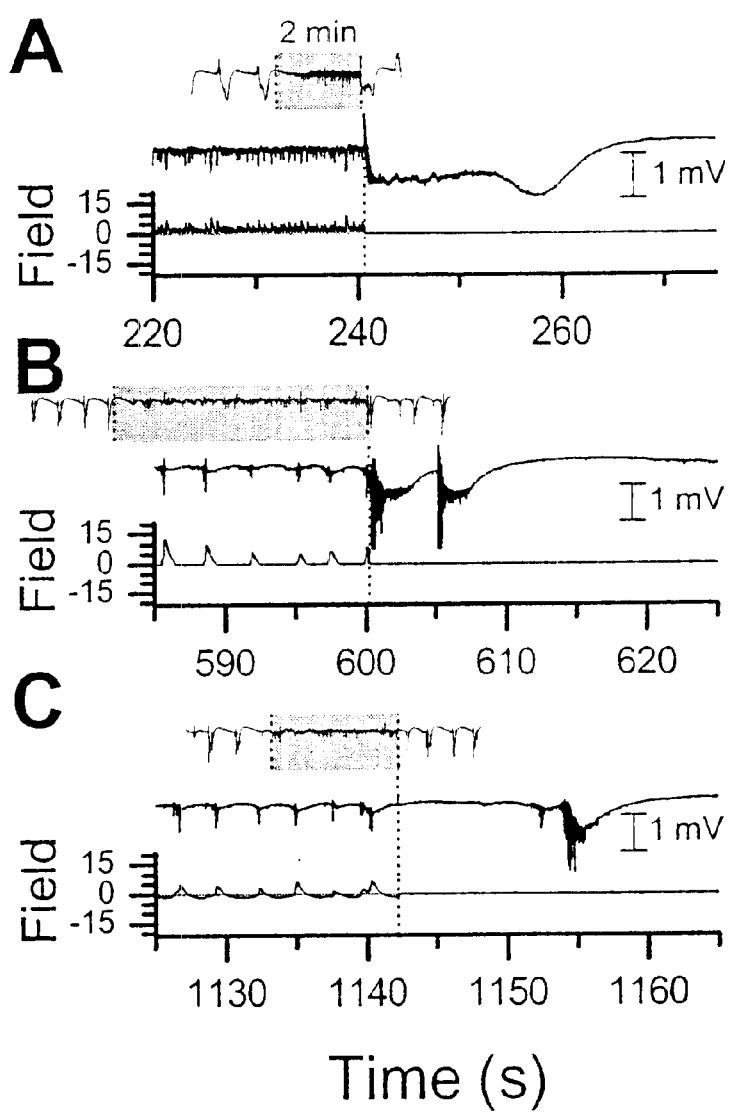
FIG. 9. Examples of network activity when control is released. In each panel, the inset is the activity for the full control period, indicated in gray, plus the baseline periods before and after. The trace in (A) corresponds to the same experiment as FIG. 3A, with half-wave rectified control. The network oscillates between excitation similar to seizure onset and being suppressed by the controller. When control is released, this activity proceeds immediately into a full seizure-like event. B,C Traces from another experiment in which half-wave rectified control (B) was compared to non-rectified control (C). For half-wave rectification, seizures were observed very soon (0–3 s) after control was released, as compared to 12–18 s for non-rectified control. The time base for the insets is the same, and indicated in (A). The inset vertical scale is half that of the main traces.

The character of the activity during control varied from experiment to experiment. It depended both on variations in the network activity as well as our choice of parameters for the controller. In some cases, (FIG. 3A), during control, the network-controller system would be in a cyclic state. The network would begin to become more excited and then the controller would apply a field, causing the neural activity to become quiet. The field would then decrease, and the cycle would repeat. In these cases, large seizure-like events were observed nearly immediately when the controller was turned off. An example of such a seizure following release is illustrated in FIG. 9A, for the same control run as FIG. 3A. The upper trace is the recorded field potentials, while the lower trace is the applied field. In other cases, the amount of intervention by the controller cycled on a longer time scale (of order a minute), often reaching a point at which no field would be applied for a few seconds. In those cases, the activity when control was released depended on the phase of this cycle. If the controller was actively suppressing when shut off, then a seizure would progress (FIG. 9B). Otherwise, one would appear later, but within a few seconds of release.

In the majority of these experiments only half-wave rectified control was used. This has the effect of only suppressing activity when it is above the threshold. If we use the full proportional feedback control signal (full-wave control), the effect is not only to suppress when the activity level is too high, but to also excite when the activity level is too low. In the two longer experiments (2 slices from 2 rats) in which we compared full-wave to half-wave rectified control with similar parameters, upon release the network was consistently quiet for a period comparable to roughly half the baseline inter-event interval. An example of full-wave release is shown in FIG. 9C for comparison with half-wave release of 9B in the same network. During this experiment, designed to contrast the network responses to these different control algorithms, we alternated solely between rectified and non-rectified control (with baseline in-between) at constant gain. The intervals between turning off control and the next event were 0.1–6 s for rectified control (3 applications) and 14–17 s (4 applications) for full signal control. Application of a Student's t test estimates these distributions to be different with greater than 95% significance. Similar results were observed for the experiment of FIG. 4.

Results Summary

Clear suppression of the seizure-like activity compared to the baseline activity during was achieved using feedback control through electric field stimulation in 20 of 30 seizing slices (4 whole transverse slices, 21 cut transverse slices, and 5 CA1 longitudinal slices; prepared from 21 rats). Half-wave control was applied in all, and full wave control was applied in 5, of the successful suppression applications. We analyzed 5 experiments in detail as described for the experiment in FIGS. 4–8. In each of those experiments, the RMS power and power fluctuation in the frequency band 100–350 Hz during control was significantly lower than during baseline recordings, as in FIG. 8C. In each, there were clear differences in the character (duration, average and maximum power) of the events as extracted from the RMS power, and 4 out of 5 revealed clear differences from events extracted from the DC deflections. In 6 experiments (6 slices from 6 rats), we maintained control for periods of at least 5 minutes without breakthrough seizures before parameters were changed. In addition, we generated seizures in non-seizing slices by applying positive feedback in 4 experiments (4 slices from 4 rats).

Control Failure

We were not always successful in controlling seizures, and the reasons for failure appear multifactorial. Procedural and equipment problems often played a role. Specifically, failure to closely align the reference electrode on the same isopotential of the applied field as the measurement electrode played a role in at least 3 of the outright failures, and prevented detailed analysis from at least another 3 experiments. The formation of large air bubbles deformed the electric field in one experiment. In three other cases, control parameters (especially the filter settings) were not found which would suppress the seizures and not respond to the background activity. This would occur for example when the events had very little of the high frequency signature at seizure initiation, so suppressive field was not applied until too late.

More interesting are some of the dynamical failures to control. In some cases of half-wave control, the activity level would be modulated by the field, but would continue to increase until the controller would saturate at the maximum allowed field amplitude. The seizure would then be free to break through, as observed with constant field application (FIG. 6A). After these 'breakthrough' seizures, the RMS activity would then decrease, and the field would return to zero. Breakthrough seizures could often be eliminated by increasing the maximum field amplitude. In four of the complete failures, breakthrough seizures were observed within one typical seizure interval of initiation of control. In four of the successful experiments, breakthrough seizures either were only observed after 3–7 minutes (3–10 seizure intervals) of control, or appeared as relatively small events compared to the uncontrolled activity. In at least three of the cases for which we failed to control the activity, subsequent multiprobe measurements of activity indicated that the seizures were initiating at points distant from where we were controlling, and were propagating toward the microelectrode.

For further aspects of neurophysiology, reference is made to Kandel and Schwartz, 4$^{th}$ Edition, and, Fundamentals of Neuroscience, Zigmond et al.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all patents and publications, cited above and in the figures are hereby incorporated in their entirety by reference.

From the foregoing description, one skilled in the art can easily ascertain the essential characteristics of this invention, and without departing from the spirit and scope thereof, can make various changes and modifications of the invention to adapt it to various usages and conditions.

References

Adair, R (1991) Constraints on biological effects of weak extremely-low-frequency electromagnetic fields. Phys. Rev. A 43:1039–1048.

Arieli A, Sterkin A, Grinvald A, Aertsen A (1996) Dynamics of ongoing activity: explanation of the large variability in evoked cortical responses. Science 273: 1868–1871

Barbarosie M, Avoli M (1997) CA3-driven hippocampal-entorhinal loop controls rather than sustains In Vitro limbic seizures, J. Neurosci. 17: 9308–9314.

Bawin S M, Abu-Assal M L, Sheppard A R, Mahoney M D, Adey W R (1986a) Long-term effects of sinusoidal extracellular electric fields in penicillin-treated rat hippocampal slices. Brain Res. 399: 194–199.

Bawin S M, Sheppard A R, Mahoney M D, Abu-Assal M, Adey W R (1986b) Comparison between the effects of extracellular direct and sinusoidal currents on excitability in hippocampal slices. Brain Res. 362: 350–354

Belair J, Glass L, an der Heiden U, Milton, J. (eds) (1995). *Dynamical Disease: Mathematical Analysis of Human Illness.* (Woodbury: AIP Press).

Bragdon A C, Kojima H, Wilson, W A (1992). Suppression of interictal bursting in hippocampus unleashes seizures in entorhinal cortex: a proepileptic effect of lowering $[K^+]_o$ and raising $[Ca_2^+]_o$. Brain Research 590: 128–135

Borck C, Jefferys, J G R (1999). Seizure-Like Events in Diinhibited Ventral Slices of Adult rat hippocampus. J. Neurophysiol. 82:2130–2142

Chan C Y, Nicholson C (1986) Modulation by applied electric fields of Purkinje and stellate cell activity in the isolated turtle cerebellum. J. Physiol. (Lond.) 371: 89–114

Chan C Y, Houndsgaard J, Nicholson C (1988) Effects of electric fields on transmembrane potential and excitability of turtle cerebellar Purkinje cells In Vitro. J. Physiol. (Lond.) 402: 751–771

Cole K S (1972) *Membranes ions and impulses* (Berkeley: Univ. California Press).

Cooper I S, Amin I, Riklan M, Waltz J M, Poon T P (1976) Chronic cerebellar stimulation in epilepsy. Arch. Neurol. 33: 559–570.

Cooper I S, Upton A R (1985) Therapeutic implications of modulation of metabolism and functional activity of cerebral cortex by chronic stimulation of cerebellum and thalamus. Biol Psychiatry 20: 811–813.

Fisher R S, Uematsu S, Krauss G L, Cysyk B J, McPherson R, Lesser R P, Gordon B, Schwerdt P, Rise M (1992) Placebo-Controlled pilot study of centromedian thalamic stimulation in treatment of intractable seizures. Epilepsia 33, 841–851.

Ghai R S, Bikson M, Durand, D M (2000) Effects of applied electric fields on low-calcium epileptiform activity in the CA1 region of rat hippocampal slices. J. Neurophysiol 84, 274–80.

Gluckman B J, Neel E J, Netoff T I, Ditto W L, Spano M L, Schiff S J (1996a) Electric field suppression of epileptiform activity in hippocampal slices. J. Neurophysiol. 76: 4202–4205.

Gluckman B J, Netoff T I, Neel E J, Ditto W L, Spano M L, Schiff S J (1996b) Stochastic resonance in a neuronal network from mammalian brain. Phys. Rev. Lett., 77: 4098–4101.

Jefferys J G R (1981) Influence of electric fields on the excitability of granule cells in guinea-pig hippocampal slices. J. Physiol. (Lond.) 319: 143–152.

Jerger K, Schiff S J (1995) Periodic pacing an In Vitro epileptic focus, J Neurophysiol. 73: 876–879.

Kayyali H, Durand D (1991) Effects of applied currents on epileptiform bursts In Vitro. Exper. Neurol. 113: 249–254.

Lesser R P, Kim S. II., Beyderman L., Miglioreti D. L., Webber W. R. S., Bare M., Cysyk B., Krauss G., Gordon B (1999). Brief bursts of pulse stimulation terminate afterdischarges caused by cortical stimulation. Neurology 53: 2073–2081.

Llinas R R, Ribary U, Jeanmonod D, Kronberg E, Mitra P P (1999) Thalamocortical dysrhythmia: A neurological and neuropsychiatric syndrome characterized by magnetoencephalography. Proc. Nat. Acad. Sci. 96: 15222–15227.

McLachlan R S (1997) Vagus nerve stimulation for intractable epilepsy: A review. Journal of Clinical Neurophysiology 14: 358–368.

Murphy J V, Hornig G, Schallert G (1995) Left vagal nerve stimulation in children with refractory epilepsy. *Arch. Neurol.* 52: 886–889.

Nakagawa M, Durand D (1991) Suppression of spontaneous epileptiform activity with applied currents. Brain Res. 567: 241–247.

Rushton WAH (1927) The effect upon the threshold for nervous excitation of the length of nerve exposed, and the angle between current and nerve. J. Physiol. (Lond.) 63: 357–377.

Rutecki P A, Lebeda F J, Johnston D (1985). Epileptiform activity induced by changes in extracellular potassium in hippocampus, J. Neurophysiol. 54: 1363–1374

Schiff S J, Jerger K, Duong D H Chang, T., Spano, M L, Ditto W L (1994). Controlling chaos in the brain. Nature 370: 615–620.

Schiff S J, Colella D, Hughes E, Conry J, Creekmore J W., Marshall A., Bozek-Kuzmicki M., Weinstein S L, Benke G., Gaillard W D, and Jacyna G M. (2000) Brain Chirps: Spectrographic Signatures of Epileptic Seizures. Clinical Neurophysiology 111, 953–958.

Staley K J, Longacher M, Bairns J S, Yee A (1998) Presynaptic modulation of CA3 network activity. Nat. Neurosci. 1: 201–209.

Terzoulo C A, Bullock T H (1956) Measurement of imposed voltage gradient adequate to modulate neuronal firing. Proc. Nat. Acad. Sci. 42: 687–694.

Tranchina D, Nicholson C A (1986) Model for the polarization of neurons by extrinsically applied electric fields. Biophys. J. 50: 1139–1159.

Traynelis S F, Dingledine R (1988) Potassium-induced spontaneous electrographic seizures in the rat hippocampal slice. J. Neurophysiol. 59: 259–276.

Van Buren J M, Wood J H, Oakley J, Hambrecht F (1978) Preliminary evaluation of cerebellar stimulation by double-blind stimulation and biological criteria in the treatment of epilepsy. J. Neurosurgery 48: 407–416.

Velasco M, Velasco F, Velasco A L, Boleaga B, Jimenez F, Brito F, Marquez I (2000) Subacute electrical stimulation of the hippocampus blocks intractable temporal lobe seizures and paroxysmal EEG activities. Epilepsia 41: 158–169.

Wadman W J, Juta A J, Kamphuis W, Somjen G G (1992) Current source density of sustained potential shifts associated with electrographic seizures and with spreading depression in rat hippocampus. Brain Res. 570: 85–91.

Warren R J, Durand D (1998) Effects of applied currents on spontaneous epileptiform activity induced by low calcium in the rat hippocampus. Brain Research 806: 186–195.

What is claimed is:

1. A method of treating epilepsy in the brain of a patient in need thereof, comprising:

measuring changes in neuronal activity in said brain within a time period, applying adaptively, in response to said measured changes in neuronal activity in said brain, a sub-threshold and oriented electric field to the brain of a patient having epilepsy in an amount effective to reduce epileptiform activity of tbe brain, wherein the electric field is applied through field eLectrodes located in a geometrical arrangement to produce said field in said brain, and the magnitude and polarity of said electric field are changed continuously in response to the measured changes in neuronal activity within said time period.

2. A method of claim 1, wherein the electric field is applied to the brain when epileptiform activity is detected through measuring electrodes.

3. A method of claim 1, wherein the applied electric field is under full-wave control.

4. A method of claim 1, wherein the applied electric field is half-wave rectified.

5. A method of claim 1, wherein the applied electric field is proportional to the measured changes in neuronal activity.

6. A method of claim 1, wherein the measuring changes in neuronal activity is performed simultaneously and continuously with the applied electric field.

7. A method of claim 1, wherein the applied field is proportional to the difference between the root-mean-square of the measured changes in neuronal activity and a predetermined threshold activity value in a predetermined frequency band.

8. A method of claim 1, wherein the measured changes in neuronal activity is represented as the root-mean-square within a frequency band of 100–500 Hz, averaged over a set time period.

9. A method of claim 1, wherein the applied electric field modifies the firing rate of the neurons in the brain.

10. A method of claim 1, wherein the field electrodes are located radially.

11. A method of treating Parkinson's disease in a patient in need thereof, comprising:

applying adaptively, in response to tremors, rigidity, or difficulty in initiating movement, a sub-threshold and oriented electric field to the brain of a patient having Parkinson's disease in an amount effective to reduce said tremors, rigidity, or difficulty in initiating movement, wherein the electric field is applied through field electrodes in contact with the brain, and the magnitude and polarity of said electric field are changed continuously in response to said tremors, rigidity, or difficulty in initiating movement within a time period.

* * * * *

UNITED STATES PATENT AND TRADEMARK OFFICE
CERTIFICATE OF CORRECTION

PATENT NO.   : 6,665,562 B2
DATED        : December 16, 2003
INVENTOR(S)  : Gluckman et al.

It is certified that error appears in the above-identified patent and that said Letters Patent is hereby corrected as shown below:

<u>Column 1</u>,
Line 8, insert
-- GOVERNMENT INTEREST

STATEMENT REGARDING GOVERNMENT RIGHTS

This invention was made with government support under NIH Grant Nos. R01MH50006 and K02MH01493 awarded by the National Institute of Health. The government has certain rights in the invention. --

Signed and Sealed this

Sixth Day of July, 2004

JON W. DUDAS
*Acting Director of the United States Patent and Trademark Office*